US00PP31278P2

(12) United States Plant Patent
Smit

(10) Patent No.: US PP31,278 P2
(45) Date of Patent: Dec. 24, 2019

(54) ***PEPEROMIA* PLANT NAMED 'EC-PEPE-1803'**

(50) Latin Name: *Peperomia albovittata*
Varietal Denomination: EC-PEPE-1803

(71) Applicant: Obed Smit, Sappemeer (NL)

(72) Inventor: Obed Smit, Sappemeer (NL)

(73) Assignee: Eden Collection BV (NL)

( * ) Notice: Subject to any disclaimer, the term of this patent is extended or adjusted under 35 U.S.C. 154(b) by 0 days.

(21) Appl. No.: 16/350,699

(22) Filed: Dec. 18, 2018

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct *Peperomia* cultivar named 'EC-PEPE-1803' is disclosed, characterized by unique, small heart shaped foliage. Leaves are distinct and striking, having dark veins on a silver-grey leaf blade. Plants form strong rosettes. The new variety is a *Peperomia*, typically used as an ornamental plant.

2 Drawing Sheets

Figure 1:
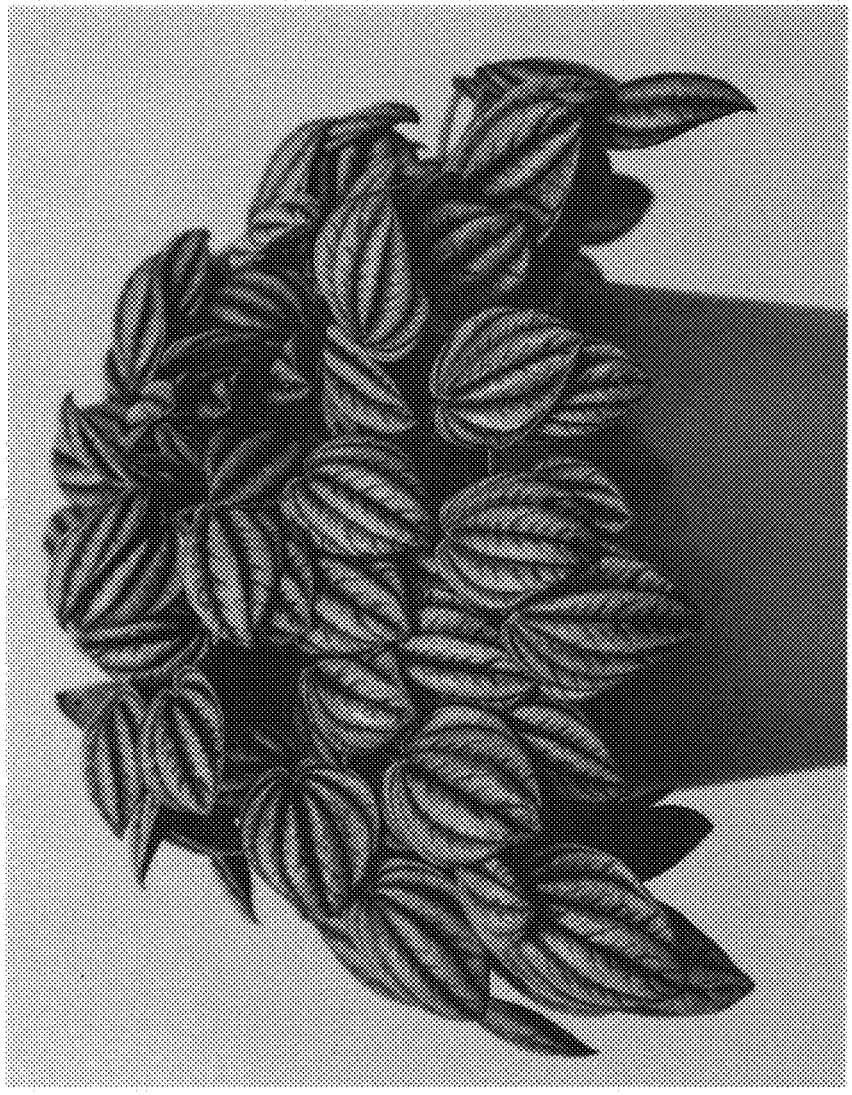

Latin name of the genus and species: *Peperomia albovittata.*

Variety denomination: 'EC-PEPE-1803'.

BACKGROUND OF THE INVENTION

The new cultivar is a product of a planned breeding program. The new variety was selected as a seedling resulting from the crossing of two unnamed, unpatented varieties of *Peperomia albovittata*. The crossing was made by the inventor, Obed J. Smit, a citizen of the Netherlands in 2014. 'EC-PEPE-1803' was selected by the inventor in September of 2015 at a commercial greenhouse in Sappemeer, the Netherlands.

Asexual reproduction of the new cultivar 'EC-PEPE-1803' by leaf cuttings was first performed in Sappemeer, the Netherlands at a commercial greenhouse in September of 2015 and has shown that the unique features of this cultivar are stable and reproduced true to type through successive generations.

SUMMARY OF THE INVENTION

The cultivar 'EC-PEPE-1803' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'EC-PEPE-1803' These characteristics in combination distinguish 'EC-PEPE-1803' as a new and distinct *Peperomia* cultivar:

1. Distinct and striking leaf pattern and color contrast of dark veins on a silver-grey leaf blade.
2. Small, compact heart-shaped leaves.

PARENT COMPARISON

Plants of the new cultivar 'EC-PEPE-1803' are similar to plants of the female parent in most horticultural characteristics, however, plants of the new cultivar 'EC-PEPE-1803' differ from in the following characteristics:

1. New cultivar has lighter green leaves.
2. New variety's leaves are smaller than the seed parent's leaves.

Plants of the new cultivar 'EC-PEPE-1803' are similar to plants of the male parent in most horticultural characteristics, however, plants of the new cultivar 'EC-PEPE-1803' differ in the following characteristics:

3. New cultivar has light green leaves with dark veins; pollen parent has brown-green leaves.
4. New variety's leaves are smaller than the pollen parent's leaves.

COMMERCIAL COMPARISON

Plants of the new cultivar 'EC-PEPE-1803' are similar to plants of the commercial variety *Peperomia marmorata* x metallica 'Eden Rosso', U.S. Plant Pat. No. 24,379. However, plants of the new cultivar differ in the following characteristics:

1. 'EC-PEPE-1803' has light green leaves with dark veins; comparator has green leaves with red veins.
2. New variety's leaf undersides are light green; comparator's leaf undersides are red.
3. 'EC-PEPE-1803' has a less elongated, more heart shaped leaf than comparator.

Plants of the new cultivar 'EC-PEPE-1803' are similar to plants of the commercial variety *Peperomia caperata* 'Napoli Nights', U.S. Plant Pat. No. 29,416. However, plants of the new cultivar differ in the following characteristics:

1. 'EC-PEPE-1803' has light green leaves with dark veins; comparator has grey-green leaves with green veins.
2. 'EC-PEPE-1803' has a less elongated, more heart shaped leaf than comparator.

BRIEF DESCRIPTION OF THE PHOTOGRAPHS

The accompanying photograph in FIG. 1 illustrates in full color a typical plant of 'EC-PEPE-1803' grown in a greenhouse. The plant approximately 30 weeks of age.

Figure 2:
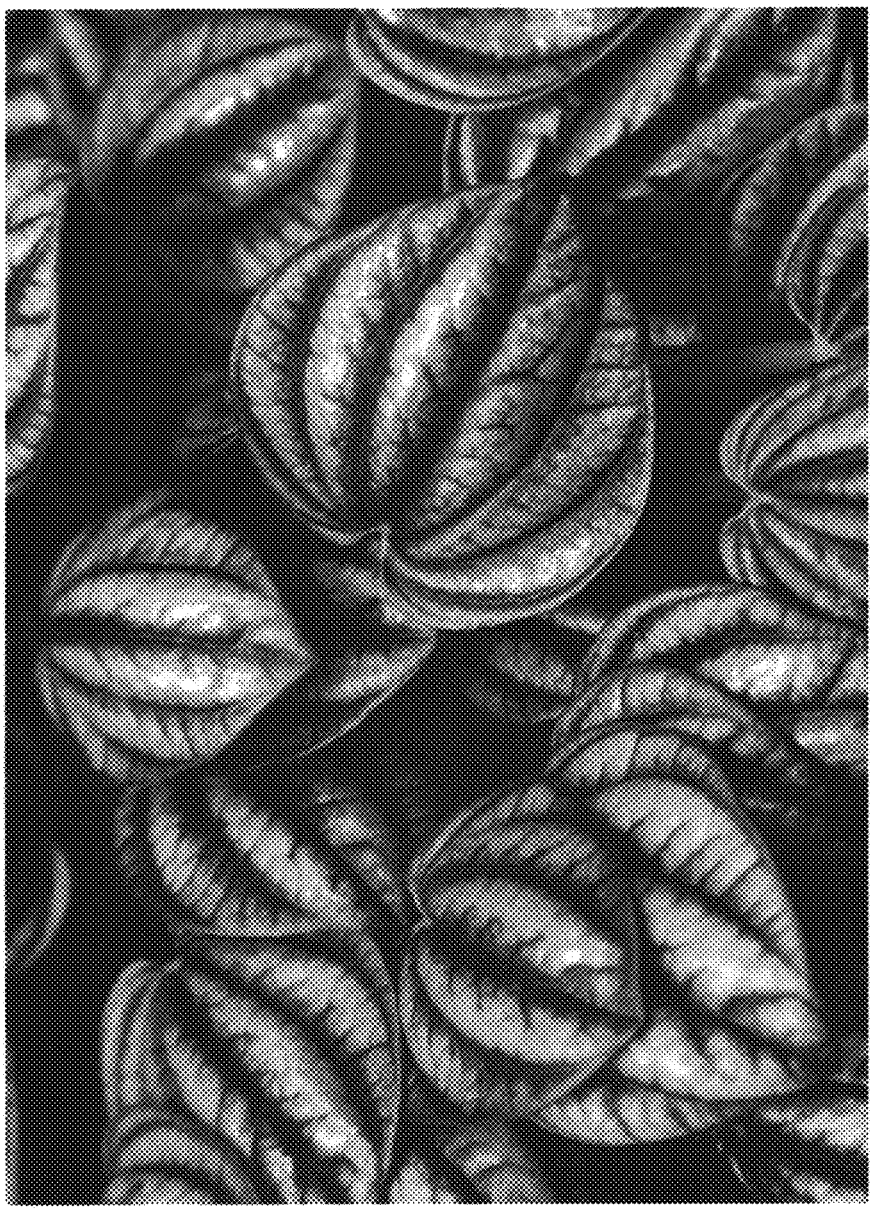

FIG. 2 illustrates a close up of the foliage. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'EC-PEPE-1803' plants grown in a greenhouse in Sappemeer, the Netherlands during February of 2018. The growing temperature ranged from 17° C. to 25° C. at night to 17° C. to 21° C. during the day. Measurements and numerical values represent averages of typical flowering types.

Botanical classification: *Peperomia albovittata* 'EC-PEPE-1803'.

Propagation:

*Time to initiate roots*.—About 10 days at approximately 20° C.

*Time to produce a rooted cutting*.—About 80 days at 20° C.

*Description of roots*.—Herbaceous, fine, freely branching.

Plant:

*Plant type*.—Tender perennial potted plant.

*Plant spread*.—Approximately 24.5 cm.

*Height*.—10.8 cm to top of foliar plane.

*Growth habit*.—Basal rosette of leaves, forming short thick stems.

*Growth rate*.—Moderate.

*Plant Vigor*.—Moderate.

*Age of Plant Described*.—Approximately 28-33 weeks from a rooted cutting.

Foliage:

*Leaf*.—Arrangement: Rosette. Quantity: Approximately 26. Average length: 4.4 cm. Average width: 3.7 cm. Shape of blade: Cordate-ovate. Apex: Acute. Base: Cordate. Margin: Entire. Aspect: Concave. Texture of top surface: Glabrous, smooth, moderately leathery. Texture of bottom surface: Glabrous, smooth, moderately leathery. Color: Young foliage upper side: RHS Yellow-Green 147B, veined greyed-purple to brown; in between N186C and 200A. Young foliage under side: Near RHS Yellow-Green 146D. Mature foliage upper side: Near RHS Greyed-Green 189A. Mature foliage under side: RHS Green to Yellow-Green; in between 138C and 147D. Venation: Type: Parallel, strongly furrowed. Venation color upper side: Mixture of RHS Yellow-Green 147A, Greyed-Purple N187A and Greyed-Green N189A. Venation color under side: Near RHS Yellow-Green 147B. Petiole: Average length: 8.4 cm. Diameter: 0.3 cm. Texture: Glabrous, smooth. Strength: Low. Color, upper and under sides: Near RHS Greyed-Orange 176A.

Flower: No flowers observed to date.

Other characteristics:

*Seeds and fruits*.—None observed to date.

*Disease/pest resistance*.—No increased nor decreased resistance to normal diseases and pests of *Peperomia* has been observed.

*Temperature tolerance*.—Tolerates temperatures from approximately 10° C. to 35° C.

What is claimed is:

1. A new and distinct cultivar of *Peperomia* plant named 'EC-PEPE-1803' as herein illustrated and described.

* * * * *